United States Patent [19]

Child et al.

[11] Patent Number: 5,386,076
[45] Date of Patent: * Jan. 31, 1995

[54] REGENERATION OF HF-BASED ALKYLATION CATALYST

[75] Inventors: Jonathan E. Child; Tomas R. Melli, both of Sewell, N.J.

[73] Assignee: Mobil Oil Corporation, Fairfax, Va.

[*] Notice: The portion of the term of this patent subsequent to Mar. 2, 2010 has been disclaimed.

[21] Appl. No.: 111,221

[22] Filed: Aug. 23, 1993

Related U.S. Application Data

[63] Continuation-in-part of Ser. No. 991,918, Dec. 17, 1992, Pat. No. 5,262,579, Ser. No. 991,919, Dec. 17, 1992, Pat. No. 5,264,650, Ser. No. 991,920, Dec. 17, 1992, Pat. No. 5,264,651, Ser. No. 991,921, Dec. 17, 1992, Pat. No. 5,264,652, and Ser. No. 991,922, Dec. 17, 1992, Pat. No. 5,276,243, each is a continuation-in-part of Ser. No. 833,684, Feb. 11, 1992, Pat. No. 5,191,150.

[51] Int. Cl.$^6$ ............................ C07C 2/62; C07C 7/10
[52] U.S. Cl. ............................ 585/802; 585/310; 585/739; 585/740; 585/752; 585/809
[58] Field of Search ............ 585/739, 740, 752, 310, 585/802; 208/60

[56] References Cited

U.S. PATENT DOCUMENTS

| | | | |
|---|---|---|---|
| 5,191,150 | 3/1973 | Child et al. | 585/809 |
| 5,262,579 | 11/1993 | Child et al. | 585/802 |
| 5,264,647 | 11/1993 | Eastman et al. | 585/724 |
| 5,264,649 | 11/1993 | Eastman et al. | 585/802 |
| 5,264,650 | 11/1993 | Better et al. | 585/802 |
| 5,264,651 | 11/1993 | Better et al. | 585/802 |
| 5,264,652 | 11/1993 | Child et al. | 585/802 |

Primary Examiner—Pal Asok
Attorney, Agent, or Firm—Alexander J. McKillop; Dennis P. Santini; Robert B. Furr, Jr.

[57] ABSTRACT

The present invention provides a method for separating conjunct polymers which are formed as byproducts of acid catalyzed isoparaffin-olefin alkylation and sulfolane from a mixture containing conjunct polymers, sulfolane, and hydrofluoric acid, which method provides a sulfolane recycle stream which requires no further drying before charging the stream to the alkylation reaction zone.

10 Claims, 3 Drawing Sheets

FIG. 2A  ASO FROM LOW DENSITY

FIG. 2B  ASO FROM HIGH DENSITY

FIG. 2C  SULFOLANE

000
REGENERATION OF HF-BASED ALKYLATION CATALYST

CROSS REFERENCE TO RELATED APPLICATIONS

This is a continuation-in-part of allowed applications Ser. No. 07/991,918, 07/991,919, 07/991,920, 07/991,921, and 07/991,922, all filed Dec. 17, 1992, now U.S. Pat. Nos. 5,262,579, 5,264,650, 5,264,651, 5,264,652 and 5,276,243 respectively, which are continuations-in-part of application Ser. No. 07/833,684, filed Feb. 11, 1992, now U.S. Pat. No. 5,191,150.

Field of the Invention

The present invention relates to the art of catalytic alkylation. More specifically, the invention relates to a liquid alkylation catalyst and an isoparaffin-olefin alkylation process. Particularly, the invention provides a liquid alkylation catalyst composition which avoids many of the safety and environmental concerns associated with concentrated hydrofluoric acid.

Background of the Invention

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used concentrated hydrofluoric or sulfuric acid catalysts under relatively low temperature conditions. Acid strength is preferably maintained at 88 to 94 weight percent by the continuous addition of fresh acid and the continuous withdrawal of spent acid. As used herein, the term "concentrated hydrofluoric acid" refers to an essentially anhydrous liquid containing at least about 85 weight percent HF.

Hydrofluoric and sulfuric acid alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Eng. Chem. Res.*, 381–397, (1988). For a survey of hydrofluoric acid catalyzed alkylation, see 1 *Handbook of Petroleum Refining Processes* 23–28 (R. A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry used anhydrous hydrogen fluoride primarily as a liquid catalyst for alkylation of olefinic hydrocarbons to produce alkylate for increasing the octane number of gasoline. Years of experience in its manufacture and use have shown that HF can be handled safely, provided the hazards are recognized and precautions taken. Though many safety precautions are taken to prevent leaks, massive or catastrophic leaks are feared primarily because the anhydrous acid will fume on escape creating a vapor cloud that can be spread for some distance. Previous workers in this field approached this problem from the standpoint of containing or neutralizing the HF cloud after its release.

U.S. Pat. Nos. 4,938,935 and 4,985,220 to Audeh and Greco, as well as U.S. Pat. No. 4,938,936 to Yan teach various methods for containing and/or neutralizing HF acid clouds following accidental releases.

But it would be particularly desirable to provide an additive which decreases the cloud forming tendency of HF without compromising its activity as an isoparaffin-olefin alkylation catalyst. Solvents and complexing agents for hydrofluoric acid have, in the past, been disclosed for various purposes as noted in the following references.

U.S. Pat. No. 2,615,908 to McCaulay teaches thioether-HF-copper complex compounds and a method for preparing the same. Potential uses for the thioether-HF-copper composition compounds are listed from column 6, line 55 through column 8 at line 3. The method is said to be useful for purifying HF-containing vent gases from an industrial HF alkylation plant. See column 7, lines 10–24.

U.S. Pat. No. 3,531,546 to Hervert discloses a HF-$CO_2$ catalyst composition which is said to be useful for alkylation as well as olefin isomerization.

U.S. Pat. No. 3,795,712 to Torck et al. relates to acid catalysts comprising a Lewis acid, a Bronsted acid, and a sulfone of the formula $R-SO_2-R'$, where R and R' are each separately a monovalent radical containing from 1 to 8 carbon atoms or form together a divalent radical having from 3 to 12 carbon atoms.

U.S. Pat. No. 3,856,764 to Throckmorton et al. teaches an olefin polymerization catalyst comprising (1) at least one organoaluminum compound, (2) at least one nickel compound selected from the class consisting of nickel salts of carboxylic acids, organic complex compounds of nickel, or nickel tetracarbonyl and (3) at least one hydrogen fluoride complex prepared by complexing hydrogen fluoride with a member of the class consisting of ketones, ethers, esters, alcohols, nitriles, and water.

U.S. Pat. No. 4,025,577 and 4,099,924 to Siskin et al. report the use of alkylation catalyst compositions containing HF, a metal halide, and sulfolane. U.S. Patent to Olah relates to an additive formulation which reduces the fuming tendency of HF.

Promoters such as alcohols, thiols, water, ethers, thioethers, sulfonic acids, and carboxylic acids are disclosed in combination with strong Bronsted acids such as HF, fluorosulfonic and trihalomethanesulfonic acids in U.S. Pat. No. 3,778,489 to Parker et al. The promoters are said to modify the activity of the strong Bronsted acids for alkylation.

The preceding references demonstrate the desirability of a liquid Bronsted acid catalyst (such as HF) for isoparaffin-olefin alkylation, as well the utility of liquid Bronsted acids in combination with metal halides, particularly metal fluorides.

Isoparaffin-olefin alkylation processes typically convert at least a portion of the feedstock to conjunct polymeric byproducts, which are more commonly referred to as acid soluble oil or ASO. Adding sulfolane to HF for isoparaffin-olefin alkylation complicates the problem of removing ASO from the system because the typical boiling range of the ASO brackets the boiling point of sulfolane (285° C., 545° F.). Thus sulfolane cannot be readily separated from ASO by distillation.

Allowed applications Ser. Nos. 07/991,919, 07/991,920, 07/991,921, and 07/991,922, as well as U.S.

Pat. No. 5,191,150 teach sulfolane recovery methods which involve reducing the HF concentration in a mixture of HF, sulfolane, and ASO to less than about 30 weight percent and then gravitationally separating the resulting for a mixture to recover sulfolane. The sulfolane-enriched stream recovered from this gravitational separation step typically contains less than about 10 weight percent water, and is preferably dried to a water content of from about 2 to about 8 weight percent water for optimum alkylation performance. Drying the sulfolane stream has, in the past, required stripping the sulfolane with an inert stripping fluid such as isoparaffin (i.e. isobutane) or nitrogen. Thus it would be desirable to simplify and still further improve the processes of allowed applications Ser. Nos. 07/991,919, 07/991,920, 07/991,921, and 07/991,922, and U.S. Pat. No. 5,191,150 by eliminating the sulfolane drying step which has been found to markedly improve alkylate quality under continuous operating conditions.

SUMMARY OF THE INVENTION

The present invention provides a method separating a mixture of HF, sulfolane, and conjunct polymeric by-products formed in HF/sulfolane-catalyzed isoparaffin-olefin alkylation, which provides a purified sulfolane stream which can be continuously recycled to the alkylation reaction zone without an intermediate drying step. The method of the invention strips a mixture of sulfolane, ASO, and hydrofluoric acid with isoparaffin for the principal purpose of removing HF from the mixture. In accordance with the invention, it has been discovered that drawing a side stream from the catalyst stripper tower eliminates the need for drying the sulfolane fraction which is produced from the downstream gravitational separation step. The stripped mixture containing sulfolane, ASO, and hydrofluoric acid then separates (in the downstream gravitational separation step) into (a) a less dense stream containing alkylate, isobutane, and a first ASO fraction; and (b) a more dense stream containing sulfolane (which requires no further drying before recycling the sulfolane to the alkylation reaction zone) and a second ASO fraction. In a preferred embodiment, the enriched overhead stream from the stripper flows to a main product fractionator, preferably entering the main product fractionator at a point above the hydrocarbon feed (which hydrocarbon feed comprises the overhead stream from the gravitational separator). It is preferable to maximize recycle of the more dense sulfolane stream to the alkylation reaction zone, and in the preferred continuous operating mode, a majority of the more dense sulfolane stream is recycled to the alkylation reaction zone.

The present invention comprises the sequential steps of:

(a) alkylating an isoparaffin with an olefin the presence of an alkylation catalyst comprising HF and sulfolane in an alkylation reaction zone whereby ASO byproduct is evolved;

(b) gravitationally separating effluent from said alkylation reaction zone to provide a less-dense stream containing alkylate product and unreacted isoparaffin and a more dense stream containing sulfolane, ASO, and HF;

(c) stripping HF from said more dense stream of step (b) with isoparaffin to provide a stripper bottoms stream containing less than about 30 percent hydrofluoric acid by weight and a stripper overhead stream containing HF, isoparaffin, a water-containing side stream, and a fraction of said ASO having a lower end boiling point than the ASO containing in said more dense stream of step (b);

(d) gravitationally separating said stripper bottoms stream into a more dense sulfolane-enriched stream and a less dense conjunct polymer-enriched stream;

(e) recycling said sulfolane-enriched stream to said alkylation reaction zone in the absence of an intermediate step to remove water from said sulfolane-enriched stream.

The method finds particular utility in regenerating an HF/sulfolane catalyst used in an isoparaffin-olefin alkylation process. The hydrofluoric acid concentration of the mixture is preferably decreased by stripping. Any suitable inert stripping fluid may be employed, including normal paraffins and isoparaffins which can be charged to the stripper tower as a vapor. Isobutane and the vaporized alkylate product formed by reacting isobutane with butene are particularly preferred stripping fluids. Two sequential stripping steps may be used, as the purity of the separated sulfolane/conjunct polymer phases improves as the hydrofluoric acid concentration decreases. If two-stage stripping is used, the enriched stripping fluid from both stripping stages is preferably charged to the product fractionator.

The effects of sequentially stripping hydrofluoric acid from the mixture before gravitational separation become particularly evident as the mixture is stripped to hydrofluoric acid levels of less than about 30 weight percent. Separation improves as the hydrofluoric acid content is decreased, with intermediate stream hydrofluoric acid concentrations preferably falling below 25 percent by weight, more preferably below about 10 percent hydrofluoric acid by weight, and most preferably below about 5 percent by weight. In a preferred embodiment, the catalyst mixture contains from about 0.5 to about 10 weight percent water.

During continuous operation, the HF/sulfolane alkylation catalyst can accumulate or lose water. Making up lost water is relatively straightforward, and water can be injected into the process at essentially any point, preferably upstream of the alkylation reactor. Drying the HF/sulfolane catalyst, on the other hand, requires a dedicated process step for removing the water. This drying step typically comprises stripping the sulfolane with an inert stripping fluid such as isoparaffin or nitrogen. Unlike the catalyst stripping step, which typically produces a useful stripper overhead stream containing isobutane enriched in HF, which can be recycled to the alkylation reaction zone, the sulfolane stripping step stream yields a wet stripping gas stream which must itself be dried before it can be recycled to the alkylation process. Thus it would be desirable to provide a method for regulating the water content of the alkylation catalyst without stripping the sulfolane stream in a separate step.

EMBODIMENTS

Figure 1:
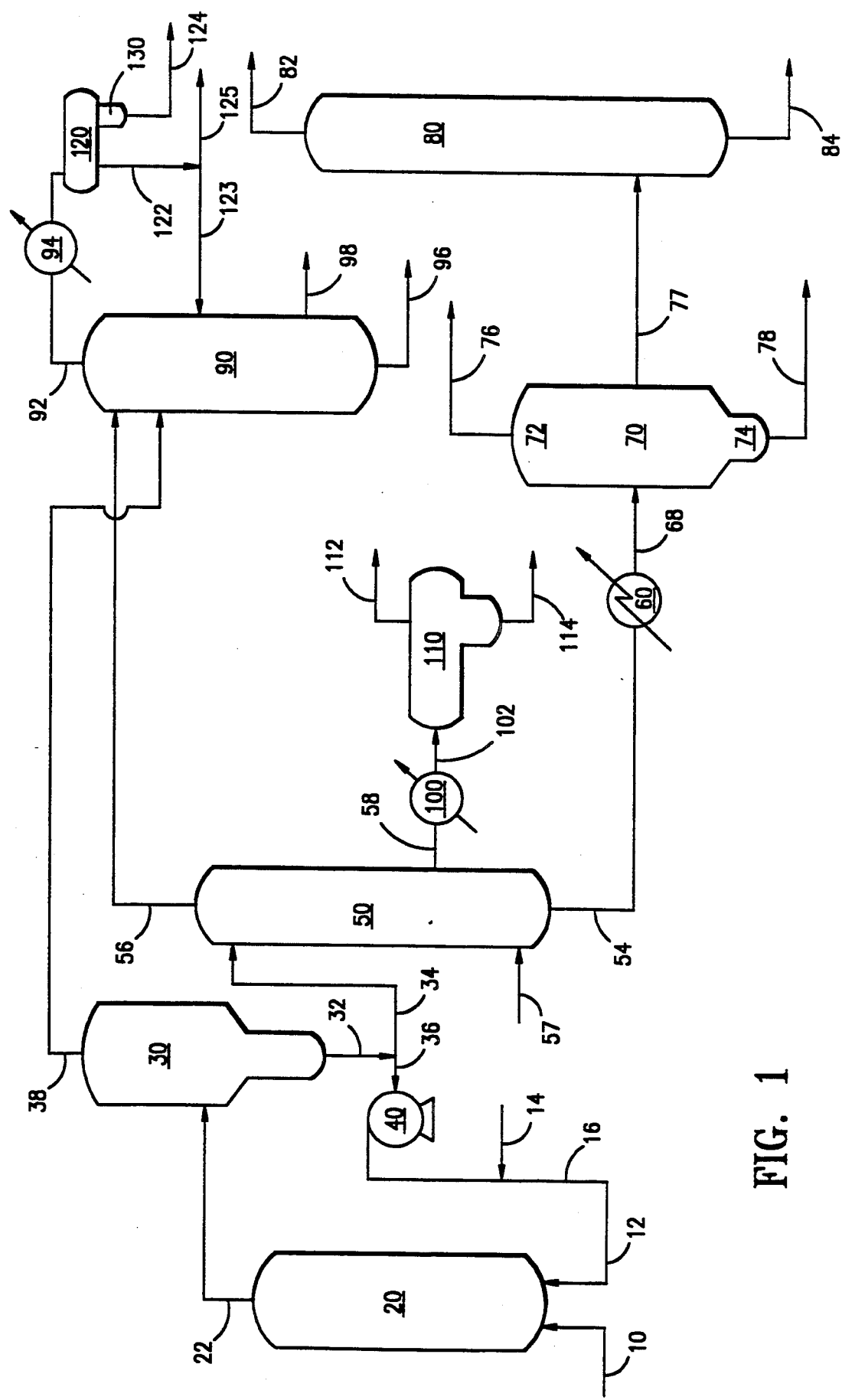
FIG. 1 is a simplified schematic diagram showing the major processing steps in the method of the invention.

Referring now to FIG. 1, mixed isoparaffin and olefin feed 10 and liquid catalyst 12 flow to riser/reactor 20. The riser/reactor effluent 22 flows to gravitational separator 30 where the effluent separates into a less dense hydrocarbon stream 38 containing alkylate and unreacted isoparaffin and a more dense catalyst stream 32 which contains HF, sulfolane, and ASO. The majority of the catalyst stream 32 recycles to riser/reactor 20 via stream 36, optionally through catalyst recycle pump 40, and stream 16. Fresh makeup HF enters stream 16 as required via stream 14. A minor amount of catalyst stream 32 flows to catalyst stripper 50 via stream 34. Isoparaffin (typically isobutane) from stream 52 strips HF and a lighter boiling fraction of the ASO from the catalyst mixture to produce a stripped catalyst stream 54 containing less than about 30 weight percent HF. The stripping fluid (isobutane), now enriched in HF and a lighter boiling fraction of the ASO, flows to product fractionator 90 as stream 56.

Vapor side draw 58, principally containing isobutane and water, condenses in side draw cooler 100 and flows as a total condensate 102 to side draw accumulator 110. The total condensate separates within side draw accumulator 110 into a less-dense hydrocarbon phase and a more-dense aqueous phase. The less-dense hydrocarbon phase, which is enriched in isobutane, is withdrawn from the side draw accumulator 110 through line 112, and the more-dense aqueous phase is withdrawn through line 114. The hydrocarbon phase may then be optionally recycled to alkylation reactor 20.

The stripped catalyst, stream 54, flows to cooler 60 from the catalyst stripper at tower temperature of about 300° F. and is cooled to about 70° F. The cooled stripped catalyst stream 68 enters gravitational separator 70 at approximately atmospheric pressure.

Two liquid phases form within gravitational separator 70. The upper, less dense phase, enriched in ASO, collects near the top 72 of gravitational separator 70, and is withdrawn through line 76 for further processing, as described below. Solids and the most dense residual hydrocarbons collect in a bottom boot 74, and are similarly withdrawn for further processing as stream 78. The lower, more dense liquid phase, enriched in sulfolane, flows out of gravitational separator 70 as stream 77, and may be recycled directly to alkylation riser/reactor 20, or may optionally be further purified, e.g., by vacuum distillation. FIG. 1 illustrates an embodiment showing the optional vacuum distillation steps. Referring again to FIG. 1, stream 77 enters a lower middle section of vacuum distillation column 80, which operates at a feed tray temperature of about 300° F. and the maximum available vacuum. The sulfolane and ASO readily separate in vacuum distillation column 80, with the sulfolane flowing overhead as stream 82 and the ASO leaving the column as stream 84. The sulfolane overhead stream 82 may then be partially or totally recycled to alkylation riser/reactor 20 with no intermediate drying step.

Streams 38 and 56 flow to product fractionator 90, with stream 56, the isobutane stripping fluid enriched in HF and a lighter boiling fraction of the ASO, preferably entering product fractionator 90 on a tray above the feed tray for stream 38. The overhead stream 92 from product fractionator 90, enriched in isobutane and HF, condenses in overhead cooler 94 and separates into a hydrocarbon phase and an acid phase in overhead accumulator 120. The hydrocarbon phase, enriched in isobutane, leaves accumulator 120 as stream 122, and splits between reflux stream 123 and isobutane recycle stream 125. The acid phase in accumulator 120 settles in the lower boot section 130 of the accumulator and is withdrawn as stream 124 for recycle to riser/reactor 20. Alkylate product, containing a minor amount of light ASO, flows from product fractionator 90 as stream 96, while n-butane is withdrawn as side draw 98.

COMPARATIVE EXAMPLE

A mixture of hydrofluoric acid, sulfolane, and conjunct polymeric byproducts (which conjunct polymeric byproducts are evolved from the catalytic alkylation of isobutane with butene, referred to hereinafter as acid soluble oil or ASO) containing about 65 weight percent hydrofluoric acid, 30 weight percent sulfolane and about 5 weight percent ASO, is charged to a decantation vessel at ambient temperature and pressure sufficient to maintain the mixture in the liquid phase. The mixture is allowed to stand for approximately 24 hours. No phase separation is observed.

EXAMPLE 1

A mixture of hydrofluoric acid, sulfolane, and ASO (having the same composition as the mixture of the Comparative Example, above) is charged to a stripping tower having three theoretical stages. Isobutane is introduced into the tower at a level below the height of the liquid (HF/sulfolane/ASO) charge point, and the isobutane and mixture charge rates are controlled to maximize stripping of HF while operating below the flooding point of the tower. A stripped liquid is withdrawn from the bottom of the tower and a HF-enriched isobutane stream is withdrawn from the top of the tower. The stripped liquid contains less than about 30 percent by weight of hydrofluoric acid.

The stripped liquid is then charged to a decantation vessel and allowed to stand for approximately 24 hours. The mixture separates into two distinct phases, an upper, less dense ASO-enriched phase, and a lower, more dense, sulfolane-enriched phase.

EXAMPLES 2–4

Additional samples of the mixture of hydrofluoric acid, sulfolane, and ASO (having the same composition as the mixture of the Comparative Example) are stripped with isobutane to hydrofluoric acid contents of 25 weight percent, 10 weight percent, and 5 weight percent, respectively. The stripped mixtures containing lower concentrations of hydrofluoric acid separate more readily than mixtures having higher HF concentrations.

EXAMPLE 5

The HF/sulfolane sample of Example 5 has the following composition:

| Component | Weight Percent |
| --- | --- |
| HF | 62 |
| Sulfolane | 27 |
| Isobutane | 4 |
| Water | 1-2 |
| ASO | 3 |
| Balance - Other Hydrocarbons | to 100% |

This mixture is a single liquid phase at 90° F. and 120 psig.

The sample is brought to atmospheric pressure and room temperature and most of the light hydrocarbons and part of the HF are vented off. Under these conditions, the sample is a single liquid phase containing about 50 wt. % HF.

Nitrogen is then bubbled through the mixture at room temperature and atmospheric pressure to strip HF off the mixture. As the mixture is depleted in HF, the mixture separates into two phases.

Both phases are analyzed, and the dense phase (specific gravity about 1.26) contains 83.2 wt. % sulfolane, 2.2 wt. % ASO, and the balance water, salts, and a sludge. The lighter phase, having a density of less than about 1, contains 82.8 wt. % ASO, 13.3 wt. % sulfolane, and the balance of salts.

Figure 2:
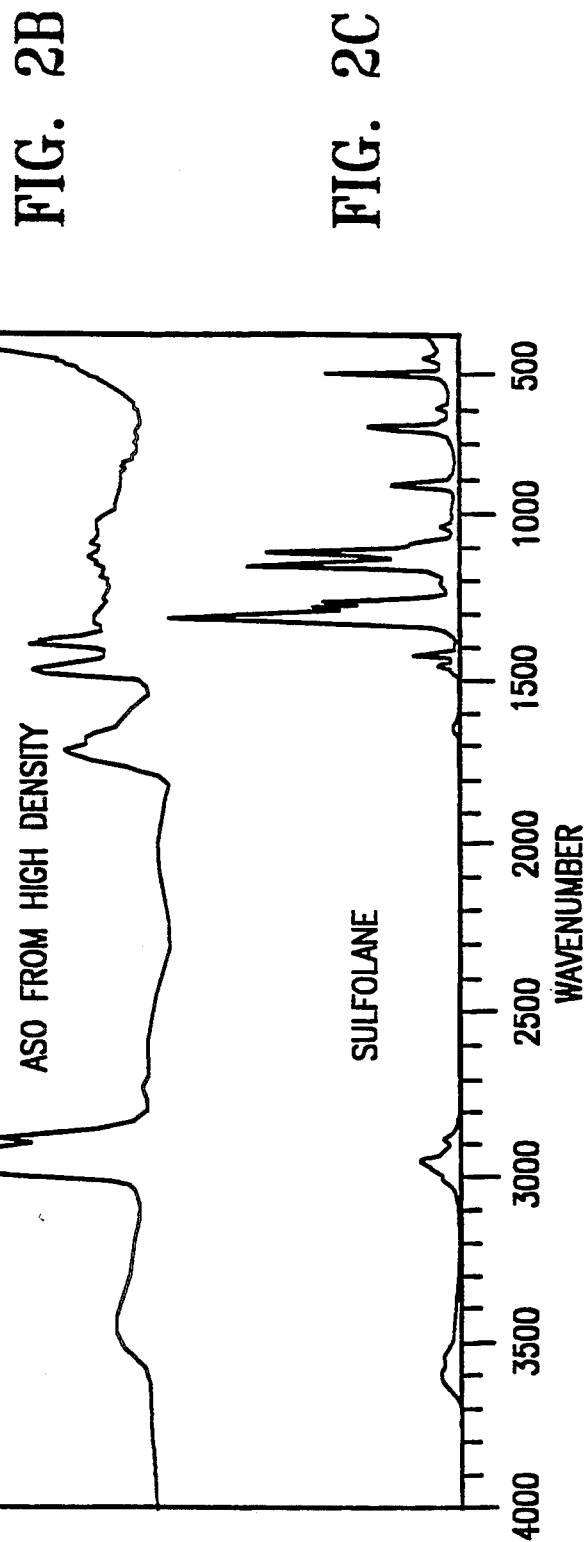
FIG. 2A shows the infrared (IR) spectrum of the conjunct polymer from the lower-density phase withdrawn from the gravitation separation step of the invention.
FIG. 2B shows the IR spectrum of the higher density phase withdrawn from the gravitational separation step of the invention.
FIG. 2C shows the IR spectrum of sulfolane extracted from the higher density phase withdrawn from the gravitational step of the invention.

FIG. 2 shows the IR spectra of ASO from the lighter phase (the upper spectrum), ASO from the heavier phase (the middle spectrum) and sulfolane (the lower spectrum).

Figure 3:
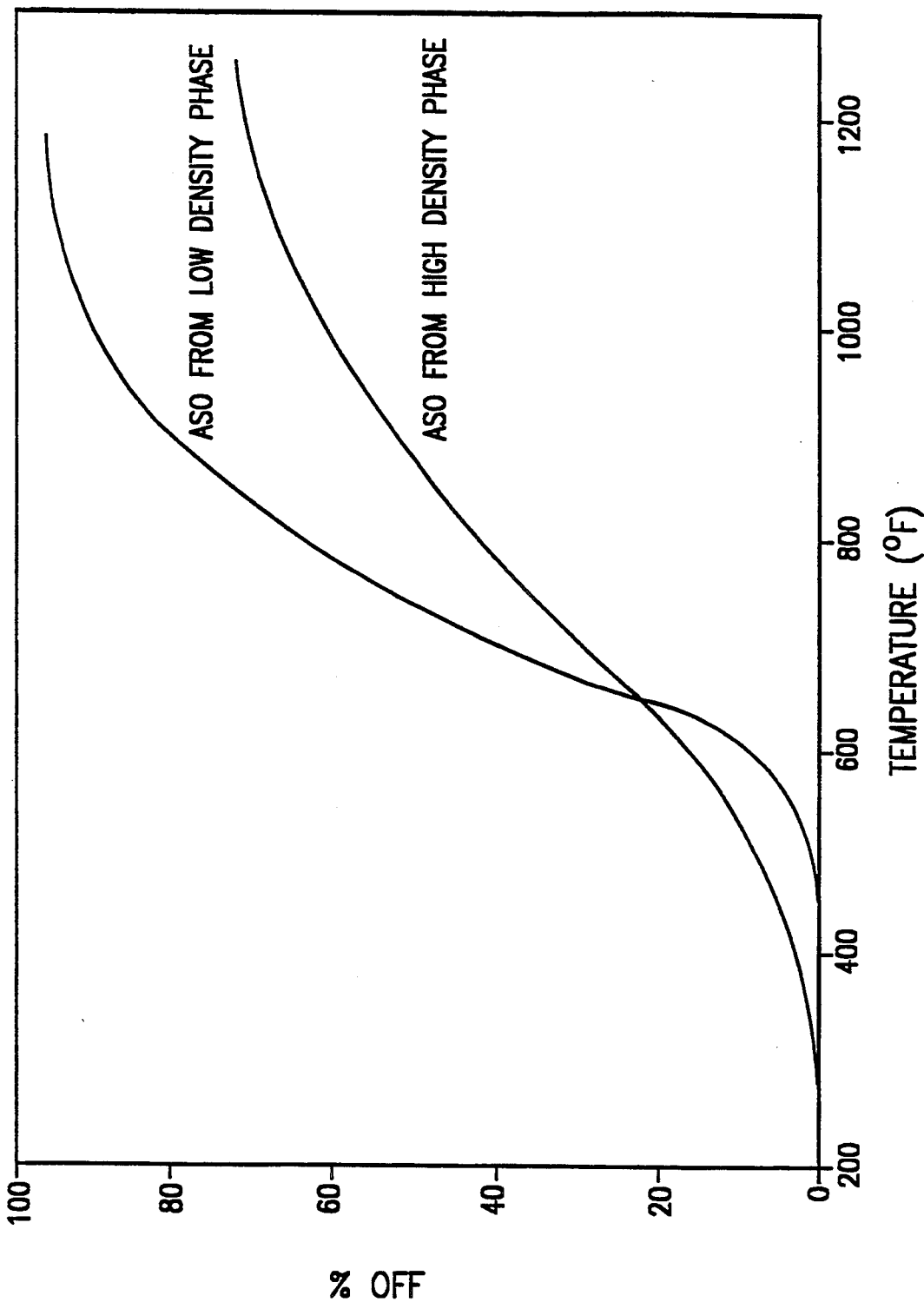
FIG. 3 shows a simulated distillation comparing the boiling ranges of components in the conjunct polymeric byproducts (also referred to herein as acid soluble oil or ASO) from the lower density phase of the gravitational separation step with the ASO from the higher density phase of the gravitational separation step of the invention.

FIG. 3 shows simulated distillations of ASO fractions from the low density phase and the high density phase from the gravitational separation step. The initial boiling point and the endpoint for the low density phase are both different from the corresponding points for the high density phase. Thus the gravitational separation splits the ASO into two fractions having different, albeit overlapping, boiling ranges.

EXAMPLE 6

The sulfolane-enriched dense phase of Example 5 is charged to a vacuum distillation column under the maximum available vacuum. The column bottom temperature is about 300° F. The overhead stream withdrawn from the distillation column is highly enriched in sulfolane while the bottoms product predominantly contains the higher boiling ASO fraction contained in the more-dense phase of Example 5.

EXAMPLE 7

A catalyst mixture containing about 65 wt. % HF, 30 wt. % sulfolane, and about 5 wt. % ASO is fed to a catalyst stripper column at a rate of about 2,000 barrels per day (BPD). The catalyst stripper column operates at about 150 psi. Isobutane (as stripping fluid) is charged to the catalyst stripper tower at a rate of about 35,000 lb/hr to strip HF and a light fraction of the ASO from the catalyst mixture. The bottom stream from the catalyst stripper tower contains approximately 82 wt. % sulfolane and the balance HF, heavy ASO, and hydrocarbons. From the top of the catalyst stripper column, about 35,000 lb/hr of isobutane, 17,000 lb/hr of HF, and 800 lb/hr of ASO at about 200° F. are sent to the an upper (stripping) section of a main product fractionator.

The principal feeds to the main product fractionator are about 950,000 lb/hr of hydrocarbon alkylation reactor effluent, which predominately comprises isobutane with about 15 wt. % alkylate. The overhead stream from the main product fractionator, about 750,000 lb. of hydrocarbon and HF, is condensed and separated into two phases: an isobutane-rich phase saturated in HF and essentially free of ASO, and an HF phase, saturated in isobutane and essentially free of ASO.

A small side stream removes n-butane from the main product fractionator. The bottoms product, mainly alkylate and ASO, is sent to an alkylate product storage tank. Of the total charge to the product fractionator, the acid-rich feed from the top of the catalyst stripper column typically accounts for about 3.5 to about 4%, and the light ASO fraction typically comprises about 0.7 wt. % of the alkylate product stream withdrawn from the product fractionator.

EXAMPLE 8

Referring now to FIG. 1, Example 8 illustrates an embodiment of the invention showing typical flowrates and stream compositions for the process streams surrounding catalyst stripper 50, side draw cooler 100, and side draw liquid accumulator 110. For the purposes of Example 8, catalyst stripper 50 is assumed to contain five tray stages with stream 34 entering the stripper column at a point above the uppermost tray. Side draw stream 58 is withdrawn as a vapor at a point above the fourth stage (counting stages from the top of the column). The isobutane stripping fluid 52 enters the catalyst stripper 50 at a point below the fifth stage (counting from the top of the column).

| | Example 8 Stream Compositions | | | | | | |
| --- | --- | --- | --- | --- | --- | --- | --- |
| Component, wt. % | Stream Number | | | | | | |
| | 34 | 52 | 54 | 56 | 58/102 | 112 | 114 |
| Isobutane | 0.0 | 100.0 | 0 | 56.3 | 86.8 | 95.0 | 0 |
| HF | 66.2 | 0 | 2.0 | 42.5 | 6.89 | 0.8 | 52.5 |
| ASO | 3.2 | 0 | 9.7 | 0 | 0.06 | 0 | 0 |
| Sulfolane | 28.42 | 0 | 87.9 | 0 | 0.3 | 0 | 2.4 |
| Water | 2.1 | 0 | 0.4 | 1.2 | 5.93 | 0.01 | 45.1 |
| Total Flowrate, lb/hr | | | 6500 | 31200 | ≈115 | ≈98 | 14.9 |

The less-dense hydrocarbon stream 112 withdrawn from side draw accumulator 110 may be recycled as feed to the alkylation reactor 20, while the HF-enriched aqueous stream 114 may be partially recycled to alkylation reactor 20 or neutralized for disposal.

Changes and modifications in the specifically described embodiments can be carried out without departing from the scope of the invention which is intended to be limited only by the scope of the appended claims.

What is claimed is:

1. A method for separating conjunct polymers which are formed as byproducts of acid catalyzed isoparaffin-olefin alkylation and sulfolane from a mixture containing conjunct polymers, sulfolane, and hydrofluoric acid comprising the sequential steps of:
   (a) gravitationally separating a mixture containing hydrofluoric acid, sulfolane, conjunct polymers formed as byproducts of acid catalyzed isoparaffin-olefin alkylation, and alkylate product formed by acid catalyzed isoparaffin-olefin alkylation to provide a less-dense stream containing alkylate product and unreacted isoparaffin and a more dense stream containing sulfolane, conjunct polymers and hydrofluoric acid;
   (b) stripping hydrofluoric acid from said more dense stream of step (a) with isoparaffin in a multistage stripper column to provide a stripper bottoms stream containing less than about 30 percent hydrofluoric acid by weight, a stripper overhead stream containing HF, isoparaffin, and a fraction of said conjunct polymers having a lower end boiling point than the conjunct polymers contained in said more dense stream of step (a), and a water-enriched side stream; and
   (c) gravitationally separating said stripper bottoms stream into a more dense sulfolane-enriched stream and a less dense conjunct polymer-enriched stream.

2. The method of claim 1 further comprising condensing and gravitationally separating said water-containing side stream of step (b) to evolve a less-dense isoparaffin-enriched stream and a more-dense aqueous stream.

3. The method of claim 1 wherein said isoparaffin of step (c) comprises isobutane.

4. The method of claim 1 wherein said stripping fluid comprises at least one selected from the group consisting of isobutane and normal butane.

5. The method of claim 1 wherein said stripping fluid comprises an alkylated product formed by reacting an isoparaffin with an olefin.

6. The method of claim 1 wherein said hydrofluoric acid stripping step (b) provides an intermediate stream containing less than about 25 percent hydrofluoric acid by weight.

7. The method of claim 6 wherein said hydrofluoric acid separation step provides an intermediate stream containing less than about 10 percent hydrofluoric acid by weight.

8. The method of claim 7 wherein said hydrofluoric acid separation step provides an intermediate stream containing less than about 5 percent hydrofluoric acid by weight.

9. The method of claim 1 further comprising distilling said sulfolane-enriched stream of step (c).

10. The method of claim 9 wherein said distillation step is carried out under at least partial vacuum.

* * * * *